United States Patent [19]

Jennings et al.

[11] 4,089,890
[45] May 16, 1978

[54] PROCESS FOR THE DIMERIZATION OF ACRYLONITRILE

[75] Inventors: James Robert Jennings; Lawrence Francis Michael Kelly, both of Runcorn, England

[73] Assignee: Imperial Chemical Industries Limited, London, England

[21] Appl. No.: 811,440

[22] Filed: Jun. 29, 1977

Related U.S. Application Data

[62] Division of Ser. No. 684,952, May 10, 1976, Pat. No. 4,059,542.

[30] Foreign Application Priority Data

May 9, 1975   United Kingdom ............... 19615/75

[51] Int. Cl.$^2$ .................. C07C 129/00; C07C 121/20
[52] U.S. Cl. .............................................. 260/465.8 D
[58] Field of Search ................................. 260/465.8 D

[56] References Cited

U.S. PATENT DOCUMENTS

| | | | |
|---|---|---|---|
| 3,225,083 | 12/1965 | McClure | 260/465.8 D |
| 3,484,475 | 12/1969 | Cornforth et al. | 260/465.8 D |
| 3,671,565 | 6/1972 | Yoo | 260/465.8 D |
| 3,726,809 | 4/1973 | Allum et al. | 252/431 P |
| 3,729,498 | 4/1973 | Masada et al. | 260/465.8 D |
| 3,732,281 | 5/1973 | Feldman et al. | 260/465.8 D |
| 3,790,617 | 2/1974 | Masada et al. | 260/465.8 D |

FOREIGN PATENT DOCUMENTS

| | | |
|---|---|---|
| 1,385,883 | 12/1964 | France. |
| 1,519,376 | 2/1968 | France. |
| 2,062,351 | 6/1971 | Germany. |
| 1,268,614 | 5/1968 | Germany. |
| 49-28491 | 7/1974 | Japan. |

*Primary Examiner*—Joseph Paul Brust
*Attorney, Agent, or Firm*—Cushman, Darby & Cushman

[57] ABSTRACT

Catalyst composition for the dimerisation of acrylonitrile comprising an organo-phosphorus compound of formula

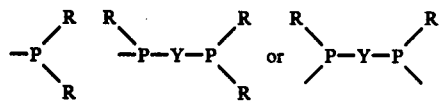

bonded to a matrix of an inorganic oxide having surface —OH groups, especially of silica or alumina. Groups R and Y are hydrocarbyl. The catalyst compositions are prepared by heating the matrix with an appropriate phosphorus compound having group(s) X which react with —OH groups with the elimination of HX. The invention also relates to a process for the dimerisation of acrylonitrile. Main products are 1,4-dicyanobutene-1 and 2-methylene glutaronitrile.

9 Claims, No Drawings

PROCESS FOR THE DIMERIZATION OF ACRYLONITRILE

This is a division of U.S. application Ser. No. 684,952 filed May 10, 1976, and now U.S. Pat. No. 4,059,542, issued Nov. 22, 1977, the entire specification and disclosure of which is hereby incorporated by reference.

This invention relates to catalyst compositions useful for the dimerisation of acrylonitrile, a process for the preparation of the compositions and a dimerisation process using such compositions as catalyst.

The dimerisation of acrylonitrile to products such as 1,4-dicyanobutene and 2-methylene glutaronitrile has been commonly catalysed by the presence of substantial or catalytic amounts of organo-phosphorus compounds, notably the tertiary phosphines, and also by certain amines.

However, such processes are usually conducted homogeneously in a liquid medium in which the phosphines are soluble under the reaction conditions, so that it may be difficult to separate the dimeric product from the phosphine catalyst.

We have now devised catalyst compositions which may be used as heterogeneous catalysts for the liquid or gas-phase dimerisation of acrylonitrile and which may be separated more readily from the dimeric products than has hitherto been possible.

According to one aspect of the present invention, a catalyst composition, suitable for use in the dimerisation of acrylonitrile, comprises a matrix of a refractory metal oxide, having chemically bonded to the surface thereof one or more organo phosphorus compounds of general formula

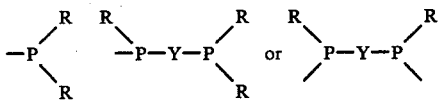

where groups R, which may be the same or different, are hydrocarbyl groups and Y represents a divalent hydrocarbyl group or a direct link, the appropriate phosphorus atom or atoms of the compound being bonded to the matrix through the oxygen atom of one or more surface hydroxyl groups of the matrix.

Hydrocarbyl groups R may be aliphatic or aromatic. Examples of suitable groups include alkyl, alkenyl, alkaryl, aralkyl, cycloalkyl or aryl groups. Although groups R are predominantly hydrocarbyl, they may contain substituent groups, for example, halogen or cyanide. Particularly suitable groups R are ethyl, phenyl and cyclohexyl.

When Y is a divalent hydrocarbyl group it is preferably a —(CH$_2$)$_n$— group where $n$ is 1, 2 or 3.

The matrix material is a finely divided refractory metal oxide which will not adversely react with the acrylonitrile or products. Examples of preferred matrix materials include silica, silica/alumina or alumina; but magnesia may also be used or may be incorporated in one of the other matrix materials. Alumina is an especially preferred material. It will be appreciated that such matrix materials commonly have hydroxyl groups bonded to their surfaces, and it is through the oxygen atoms of these that the phosphorus atoms in our compositions are bonded to the surface of the matrix.

According to another aspect of our invention, we provide a process for the preparation of a catalyst composition in which a matrix of a refractory metal oxide (as hereinbefore defined) having surface hydroxyl groups, is reacted with a phosphorus compound of general formula

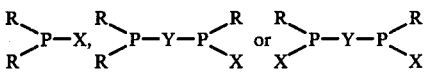

where R and Y have the same significance as before and X is a group capable of reacting with the hydrogen atom of a surface hydroxyl group to cause the phosphorus atom to which X was originally attached to bond to the matrix via the oxygen atom of the said hydroxyl group with elimination of compound HX, and the catalyst composition treated to remove any free phosphorus compound.

Examples of suitable groups X include anionic groups such as alkoxide, amide, chloride, bromide and iodide.

Without prejudice to the present invention, it is thought that the above reaction proceeds as illustrated by the following general equation

where R and X have the significance previously ascribed to them and Matrix) — OH represents a matrix material having hydroxyl groups bonded to its surface. For example, when group X is an alkoxide HX would be an alcohol; but when X is an amide HX would be a secondary amine. When the reaction is complete, the compound HX and excess unreacted phosphorus compound is removed, e.g. by washing with a suitable solvent. For example, when methoxy diphenyl phosphine was treated with finely divided silica, the catalyst composition produced was examined by infra-red spectroscopy, absorption bands were observed in the region 950 to 1090 cm$^{-1}$. These were considered to be typical of P—O—Si linkages. Excess methoxy diphenyl phosphine was not observed.

In order to control the —OH group concentration on the surface of the matrix before reaction with the phosphorus compound, it is preferably heated at a temperature in the range 100° to 700° C, and more preferably in the range 150° to 600° C. The temperature and duration of this heating will depend upon the —OH group concentration which is desired.

A solution of the phosphorus compound in a hydrocarbon solvent is heated with the matrix material to effect the reaction. Preferably heating is achieved by refluxing the mixture. It will thus be appreciated that choice of hydrocarbon solvent will depend both of the solubility of the particular phosphorus compound in the solvent and on its boiling point. Examples of suitable solvents include hexane, toluene and petroleum ether.

When the reaction between the phosphorus compound and the matrix is complete, the resultant catalyst composition is separated from the reaction mixture, e.g. by filtration. The composition is then washed with fresh solvent until the washings are free of phosphorus, and may be conveniently stored under an inert atmosphere, e.g. nitrogen.

According to yet another aspect of the present invention, we provide a process for the dimerisation of acrylonitrile in which the acrylonitrile is contacted at elevated temperature with a catalyst composition comprising a matrix of a refractory metal oxide (as hereinbefore defined), having chemically bonded to the surface thereof one or more organo-phosphorus compounds of general formula

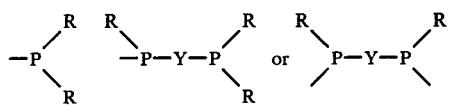

where R and Y have the meanings previously ascribed to them, the appropriate phosphorus atom or atoms of the compound being bonded to the matrix through the oxygen atom of one or more surface hydroxyl groups of the matrix.

The acrylonitrile may be in the liquid or vapour phase and, especially when used in liquid phase, may be dissolved in a suitable solvent, e.g. methoxy ethanol or tertiary butanol. However, the acrylonitrile is preferably brought into contact with the catalyst in the vapour phase to obviate separation of the product from the catalyst. The catalyst may take the form of a fixed or a fluid bed through or over which acrylonitrile vapour is passed so that the acrylonitrile/dimeric product issuing from the reactor is substantially free of catalyst.

The reaction is carried out at a temperature in the range 100° to 300° C and, preferably in the range 150° to 210° C. Normally atmospheric pressure is adequate; but it is convenient in vapour phase working to use an inert gas, e.g. nitrogen, at slightly elevated pressure to drive the vapour and/or products through the reactor. However, the use of higher pressures is not precluded, should this prove desirable.

When working in the vapour phase the issuing vapour stream is cooled to cause the dimers to condense out preferentially. The product may then be further purified by fractional distillation. When the reaction is conducted in the liquid phase, the catalyst is first separated from the acrylonitrile/product mixture and the product then separated and purified by fractional distillation. In either procedure, the unreacted acrylonitrile may be recycled.

In order to minimise the production of undue amounts of polymer from the acrylonitrile, it may be desirable to use a polymerisation inhibitor in the practice of our invention. For example an inhibitor, such as p-tertiarybutyl catechol or hydroquinone, may be added in an amount equivalent to 0.001 to 0.5% by weight based on acrylonitrile.

The so-called "promoters", for example alkanols, frequently used in acrylonitrile dimerisation processes are not usually necessary in our process; but they may be added if desired.

The dimeric products of our process will normally consist mainly of cis and trans 1,4-dicyanobutene-1 and 2-methylene-glutaronitrile, that is to say, a mixture of straight-chain and branched dimers. The relative proportions of branched and unbranched dimers will depend upon several factors, such as temperature of reaction, but we have found that a pronounced factor is the composition and form of the catalyst. For example, when mainly unbranched dimers are required it is preferred that electron with-drawing groups are bound to the phosphorus atoms. Examples of such groups are phenyl, tolyl, cyanoethyl and chlorophenyl and fluoroorganic groups. This is exemplified by the fact that when the catalyst comprises a phenylethyl phosphorus compound bound to silica or alumina, the dimeric product may contain <10% of 1,4-dicyanobutene-1; but when the equivalent diphenyl compound is used the product has >50% of 1,4-dicyanobutene-1. In each case the 1,4-dicyanobutene is almost entirely in the "cis" form.

In addition to the dimeric products, polymeric by-products are also formed; but these may be readily separated from the desired dimeric products. The contact time between the acrylonitrile and the catalyst composition may also affect the product distribution. However, the required contact time to produce the most suitable product distribution may be readily determined by experiment.

As previously mentioned the form of the catalyst may also be modified by controlling the heat treatment of the matrix material before reacting it with the phosphorus compound, and this in turn may affect the distribution of the dimeric products. For example, when silica is used as matrix and the heat treatment temperature is varied within our preferred range, i.e. 150°–600° C, increasing the heat treatment temperature increases the proportion of linear dimers (e.g. 1,4-dicyanobutene-1) in the product.

Dimers of acrylonitrile have a number of applications. For example, they may be hydrogenated to yield diamines which may be used in the production of polyamides. Thus hydrogenation of the isomers of 1,4-dicyanobutene yield hexamethylene diamine which is manufactured on a large scale as an intermediate in the production of nylon 6,6.

2-Methylene glutaronitrile is also useful as a chemical intermediate, for example as described by Moormeier and Feldman in "Hydrocarbon Processing" December 1965 44 No. 12 page 151.

It will be appreciated that the process can be operated continuously by separating the dimeric products from the gaseous effluent and recycling the acrylonitrile vapour after suitable make-up.

The invention will now be illustrated by the following Examples.

Preparation of Catalyst Compositions A to D

A solution of the appropriate phosphorus compound was prepared by stirring the compound (32 parts) in hexane (300 parts) under nitrogen until it was dissolved. Finely divided silica (54 parts), which had been heated in a muffle furnace at 300° C for 12 hours and cooled under nitrogen, was then added to the hexane solution which was then refluxed for 6 hours, at the end of which time it was allowed to cool and stood for a further 12 hours. The resulting catalyst slurry was then filtered, washed with hexane until the washings were free from phosphorus, and then dried under vacuum. Silica was treated in this way with the following phosphorus compounds A. Diphenyl isopropoxyl phosphine $(C_6H_5)_2POCH(CH_3)_2$
B. Phenylethyl isopropoxyl phosphine $(C_6H_5)(C_2H_5)POCH(CH_3)_2$
C. Diethylamino phenylethyl phosphine $(C_2H_5)_2NP(C_6H_5)(C_2H_5)$
D. Diethylamino dicyclohexyl phosphine $(C_2H_5)_2NP(C_6H_{11})_2$ The resulting catalytic compositions may be represented as follows for the sake of convenience.

A. $(C_6H_5)_2$P-O-silica
B. $(C_6H_5)(C_2H_5)$P-O-silica
C. $(C_6H_5)(C_2H_5)$P-O-silica
D. $(C_6H_{11})_2$P-O-silica In each of the above catalyst compositions the phosphorus content was found to be of the order of 2% by weight.

EXAMPLE 1

Liquid acrylonitrile was pumped into a closed vessel and heated to 170° C to convert the liquid to vapour. A stream of nitrogen was then passed through the vessel at 100 psig to force the vapour through a bed of catalyst A maintained at 170° C by external heating, with a residence time of several minutes. The effluent stream was analysed by means of gas-liquid chromatography (GLC), the product distribution being as follows

|  | cis 1,4-dicyanobutene-1 | 65% |
|---|---|---|
|  | 2-methylene glutaronitrile | 25% |
|  | trans 1,4-dicyanobutene-1) | 10% |
| and | dicyano cyclobutane) |  |

The stream was then cooled to 20° C to cause the dimeric products to condense, the condensate being equivalent to a conversion of about 7% by weight of the acrylonitrile feed.

The products were collected in a receiving vessel and the 1,4-dicyanobutene-1 was separated and purified by fractional distillation.

EXAMPLES 2-4

Catalyst compositions were prepared using the general procedure described above with diphenyl methoxyl phosphine $(C_6H_5)_2PO\ CH_3$ as the phosphine. However, the silica matrix material was heat-treated before reaction with the phosphine by heating for 24 hours under a stream of nitrogen in a silica tube at the temperature specified below. It was then cooled under nitrogen and reacted with the phosphine using the procedure already described.

Catalysts were prepared using samples of silica heated at three different temperatures. These catalysts were then used to catalyse the dimerisation of acrylonitrile by the process of Example 1. GLC analysis of the product showed that it comprised a mixture of cis 1,4-dicyanobutene-1 (DCB) and 2-methylene glutaronitrile (MGN), the proportions of the two depending on the heat-treatment of the silica matrix.

The results are set out in Table 1 below:

Table 1

| Example | Temp of Heat treatment (° C) | Ratio cis 1,4 DCB: 2-MGN |
|---|---|---|
| 2 | 150 | 20 : 80 |
| 3 | 300 | 40 : 60 |
| 4 | 490 | 65 : 35 |

EXAMPLE 5

Nitrogen was bubbled slowly through acrylonitrile to produce a stream of nitrogen containing ACN vapour. This stream was then passed through a fixed bed of Catalyst B maintained at a temperature of 190° C. The product stream was cooled in liquid nitrogen and subsequently liquified and analysed by GLC. This showed that there had been a 20% conversion of ACN, the ratio of branched to linear dimers being 90:10.

EXAMPLE 6

A further catalyst composition was prepared using the general procedure of Example 1 but with alumina instead of silica. The finely divided alumina was dried at 400° C for 12 hours and then cooled under an atmosphere of nitrogen. The alumina was then reacted with phosphorus compound A and the resulting composition washed to remove unreacted phosphorus compound. The composition was then used to dimerise acrylonitrile using the procedure of Example 1. Analysis of the effluent stream of GLC showed that it comprised 1,4-dicyanobutene-1 and 2-methylene glutaronitrile in the ratio 75:25.

What we claim is:

1. A process for the dimerisation of acrylonitrile, comprising:
   contacting acrylonitrile at a temperature in the range of 100° to 300° C with a catalyst composition consisting essentially of a matrix of a refractory metal oxide having chemically bonded to the surface thereof one or more organo-phosphorus radicals of general formula:

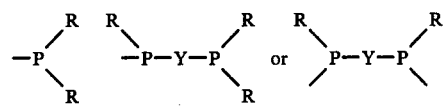

where groups R, which may be the same or different, represent hydrocarbyl groups and Y represents either a divalent hydrocarbyl group or a direct link, the appropriate phosphorus atom or atoms of the radical being bonded to the matrix through the oxygen atom of one or more surface hydroxyl groups of the matrix.

2. A process as claimed in claim 1 which is conducted at a temperature in the range 150° to 210° C.

3. A process as claimed in claim 1 in which the catalyst composition takes the form of a fixed or fluid bed over or through which the acrylonitrile is passed in liquid or vapour phase.

4. A process for the dimerisation of acrylonitrile, consisting of:
   contacting acrylonitrile at a temperature in the range of 100° to 300° C with a catalyst composition consisting essentially of a matrix of a refractory metal oxide having chemically bonded to the surface thereof one or more organophosphorus radicals of general formula:

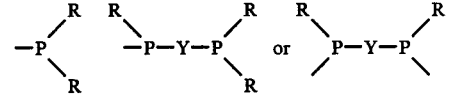

where groups R, which may be the same or different, represent hydrocarbyl groups and Y represents either a divalent hydrocarbyl group or a direct link, the appropriate phosphorus atom or atoms of the radical being bonded to the matrix through the oxygen atom of one or more surface hydroxyl groups of the matrix.

5. A process as claimed in claim 4 which is conducted at a temperature in the range 150° to 210° C.

6. A process as claimed in claim 4 in which the catalyst composition takes the form of a fixed or fluid bed over or through which the acrylonitrile is passed in vapour phase.

7. A process as claimed in claim 4 in which the catalyst composition takes the form of a fixed or fluid bed over or through which the acrylonitrile is passed in liquid phase.

8. A process as claimed in claim 4 in which the catalyst composition takes the form of a fixed or fluid bed in which the acrylonitrile, dissolved in a solvent, is passed in liquid phase.

9. A process as claimed in claim 4 in which the catalyst composition takes the form of a fixed or fluid bed over or through which the acrylonitrile is passed in vapour phase in the presence of an inert gas.

* * * * *